(12) United States Patent
Lee et al.

(10) Patent No.: US 8,834,812 B2
(45) Date of Patent: Sep. 16, 2014

(54) MICROFLUIDIC DEVICE

(75) Inventors: Yong Koo Lee, Yongin-si (KR); Na Hui Kim, Suwon-si (KR); Jong Gun Lee, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 188 days.

(21) Appl. No.: 13/370,991

(22) Filed: Feb. 10, 2012

(65) Prior Publication Data

US 2012/0207654 A1 Aug. 16, 2012

(30) Foreign Application Priority Data

Feb. 15, 2011 (KR) .......................... 10-2011-0013327

(51) Int. Cl.
*B01L 99/00* (2010.01)
*G01N 21/07* (2006.01)
*B01L 3/00* (2006.01)

(52) U.S. Cl.
CPC ............ *G01N 21/07* (2013.01); *B01L 3/50273* (2013.01); *B01L 3/502738* (2013.01); *B01L 2200/027* (2013.01); *B01L 2200/0605* (2013.01); *B01L 2200/0647* (2013.01); *B01L 2200/0684* (2013.01); *B01L 2200/10* (2013.01); *B01L 2200/14* (2013.01); *B01L 2200/16* (2013.01); *B01L 2300/022* (2013.01); *B01L 2300/024* (2013.01); *B01L 2300/0806* (2013.01); *B01L 2300/1861* (2013.01); *B01L 2400/0409* (2013.01); *B01L 2400/0677* (2013.01); *B01L 2400/084* (2013.01)
USPC .......................................................... 422/506

(58) Field of Classification Search
CPC ............................................... B01L 2400/0409
USPC .......................................... 422/502, 503, 506
See application file for complete search history.

(56) References Cited

U.S. PATENT DOCUMENTS

| 5,173,262 A | 12/1992 | Burtis et al. | |
| 6,063,589 A * | 5/2000 | Kellogg et al. | ................. 435/24 |
| 6,632,399 B1 * | 10/2003 | Kellogg et al. | ................. 422/72 |
| 2009/0317896 A1 | 12/2009 | Yoo | |

* cited by examiner

*Primary Examiner* — Paul Hyun
(74) *Attorney, Agent, or Firm* — Sughrue Mion, PLLC (57) ABSTRACT

A microfluidic device having a chamber with a fluid discharge configuration is provided. The microfluidic device includes a platform including a chamber configured to accommodate a fluid therein. The chamber includes an inner sidewall and an outer sidewall disposed outwardly from the inner sidewall in a radial direction of the platform. The outer sidewall includes a first point located closest to a center of the platform, and a second point located farthest from the center of the platform. A distance from the center of the platform to an arbitrary third point on the outer sidewall between the first point and the second point increases from the first point to the second point, so that the fluid near the first point is guided to the second point by centrifugal force during rotation of the platform.

13 Claims, 6 Drawing Sheets

MICROFLUIDIC DEVICE

CROSS-REFERENCE TO RELATED APPLICATION

This application claims priority from Korean Patent Application No. 10-2011-0013327, filed on Feb. 15, 2011 in the Korean Intellectual Property Office, the disclosure of which is incorporated herein by reference.

BACKGROUND

1. Field

Apparatuses and methods consistent with exemplary embodiments relate to a microfluidic device having a chamber with a discharge configuration to discharge all fluid accommodated in the chamber.

2. Description of the Related Art

A lab-on-a chip refers to a device in which microfluidic structures are arranged in a chip-shaped substrate to implement multiple steps of processing and operations, in order to implement tests including biochemical reactions on a small chip.

Transferring a fluid in microfluidic structures may require a drive pressure, such as capillary pressure or pressure produced by a separate pump. Recently, disc-type microfluidic devices, in which microfluidic structures are arranged on a disc-shaped platform to enable centrifugal movement of fluid, have been suggested to implement a series of operations. Such a disc-type microfluidic device is called a lab compact disc (CD), lab-on a disc or digital bio disc (DBD), discriminately with a lab-on-a chip.

Examples of microfluidic structures include chambers to confine a fluid therein, channels to provide fluid flow, and valves to control flow of a fluid. A microfluidic device may be constructed by various combinations of microfluidic structures.

When a microfluidic device is used to test a sample, test results may be sensitive to the amount of a fluid to be tested. Thus, if the amount of a fluid used in a test differs from a preset amount required for testing, this may cause erroneous test results.

As such, when centrifugal force is used on a microfluidic device, a fluid accommodated in a chamber of the device may discharged from the chamber by the centrifugal force. In particular, if the fluid accommodated in the chamber has been metered to a preset amount for a subsequent process, it may be necessary to discharge all the fluid in the chamber.

SUMMARY

Exemplary embodiments provide a microfluidic device having a chamber with a discharge configuration to discharge all fluid accommodated in the chamber.

In accordance with an aspect of an exemplary embodiment, there is provided a microfluidic device including a platform including a chamber configured to accommodate a fluid therein, the chamber including an inner sidewall and an outer sidewall disposed outwardly from the inner sidewall in a radial direction of the platform, wherein the outer sidewall includes a first point located closest to a center of the platform, a second point located farthest from the center of the platform, and wherein a distance from the center of the platform to an arbitrary third point on the outer sidewall between the first point and the second point increases from the first point to the second point, so that the fluid near the first point is guided to the second point by centrifugal force during rotation of the platform.

The chamber may further include an exit provided at the second point for outflow of the fluid accommodated in the chamber.

The chamber may further include a bottom surface that is inclined upward to the exit.

The first point and the second point may be located respectively at opposite ends of the outer sidewall.

The chamber may be a metering chamber to supply a predetermined amount of fluid to the outside.

The chamber may be formed along a circumference at a predetermined radius from the rotational center of the platform.

The inner sidewall may be formed along a circumference at a predetermined radius from the rotational center of the platform, and a distance between the inner sidewall and the outer sidewall in the radial direction of the platform may increase from the first point to the second point.

Centrifugal force applied to the second point may be greater than centrifugal force applied to the first point during rotation of the platform.

In accordance with an aspect of another exemplary embodiment, there is provided a microfluidic device including a disc-shaped platform a disc-shaped platform including a chamber configured to accommodate a fluid therein, wherein the chamber comprises an outer sidewall defining an outer wall of the chamber in a radial direction of the platform, and wherein a distance from a center of the platform to an arbitrary point on the outer sidewall increases from a first end of the outer sidewall to a second end of the outer sidewall.

The chamber may further include an exit provided at the other end of the outer sidewall.

The depth of the chamber near the exit may decrease closer to the exit.

The chamber may be a metering chamber to enable outflow of a predetermined amount of fluid to the outside.

The chamber may have an arc shape that extends in a circumference at a predetermined radius from the rotational center.

The chamber may further include an inner sidewall located inwardly from the outer sidewall in the radial direction of the platform, the inner sidewall being formed along a circumference at a predetermined radius from the rotational center, and the distance between the inner sidewall and the outer sidewall in the radial direction of the platform may increase from one end to the other end of the outer sidewall.

BRIEF DESCRIPTION OF THE DRAWINGS

The above and/or other aspects will become apparent and more readily appreciated from the following description of exemplary embodiments, taken in conjunction with the accompanying drawings of which.

DETAILED DESCRIPTION

Reference will now be made in detail to an exemplary embodiment, examples of which are illustrated in the accompanying drawings, wherein like reference numerals refer to like elements throughout.

Figure 1:
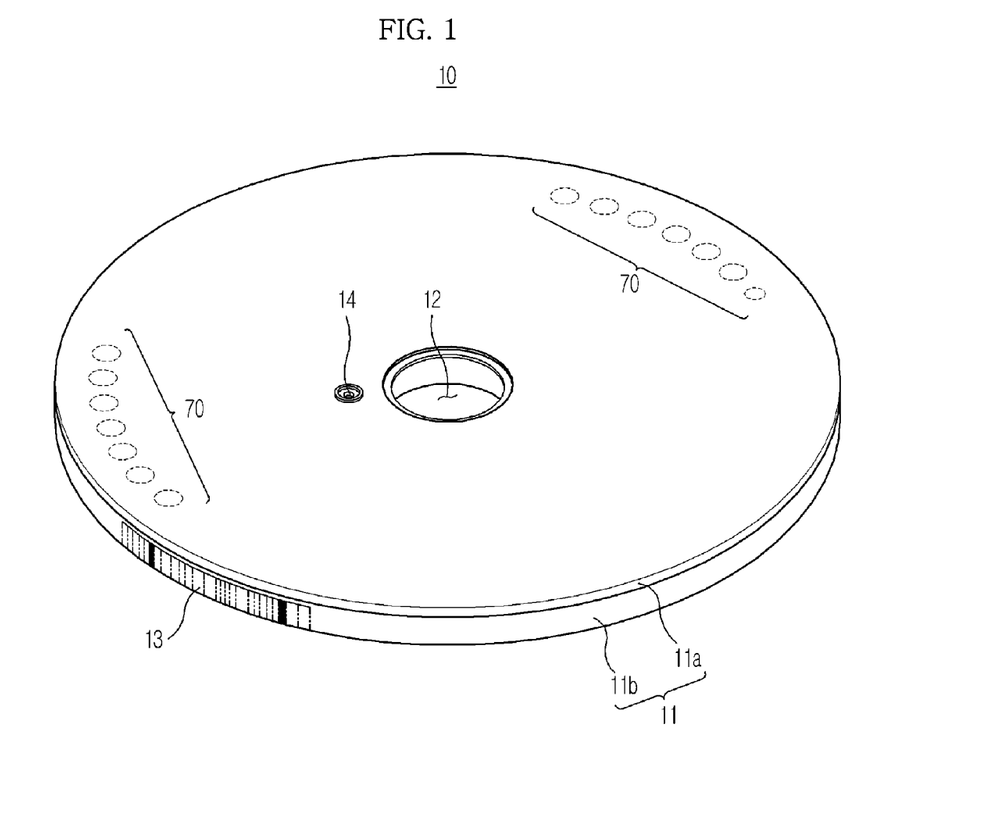
FIG. 1 is a perspective view illustrating the external appearance of a microfluidic device according to an exemplary embodiment.
Figure 2:
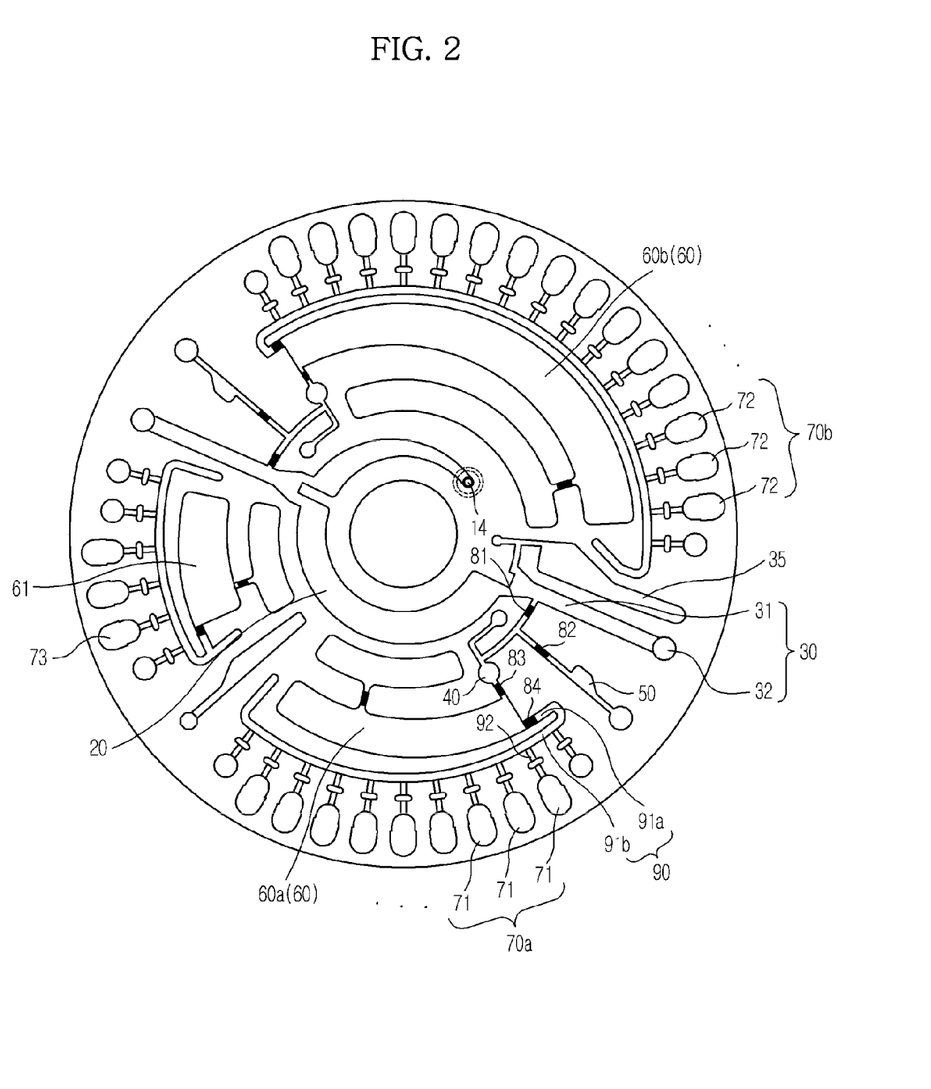
FIG. 2 is a plan view illustrating the internal configuration of a microfluidic device according to an embodiment.

FIG. 1 is a perspective view illustrating the external appearance of a microfluidic device according to one embodiment, and FIG. 2 is a plan view illustrating the internal configuration of the microfluidic device according to one embodiment.

As illustrated in FIGS. 1 and 2, the microfluidic device 10 includes a rotatable disc-shaped platform 11, a plurality of chambers for fluid accommodation and a plurality of channels for fluid flow, which are defined in the platform 11, and a barcode 13 provided at a lateral surface of the platform 11.

The platform 11 is rotatable about a center 12 thereof. The chambers and channels provided in the platform 11 may perform movement, centrifugal separation and/or mixing of a sample under the influence of centrifugal force generated by rotation of the platform 11.

In an exemplary embodiment, the platform 11 may be formed of plastics which are easy to mold and have biologically inert superficial properties, such as acryl, polydimethylsiloxane (PDMS). However, the platform 11 is not limited to this embodiment and may be formed of other materials having chemical and biological stability, excellent optical transparency and mechanical workability.

The platform 11 may be constructed from multilayered plates. The platform 11 may provide spaces and passages by forming intaglio structures corresponding to chambers, channels, etc., at interfaces of contact plates and bonding the plates to each other.

For example, the platform 11 may consist of a first substrate 11a and a second substrate 11b attached to the first substrate 11a, or may include first and second plates 11a and 11b with a partition (not shown), which defines chambers for fluid accommodation and channels for fluid flow, interposed therebetween. Additionally, the platform 11 may have various other configurations. The first substrate 11a and the second substrate 11b may be formed of thermoplastic resins.

Bonding of the first substrate 11a and the second substrate 11b to each other may be accomplished by various methods, such as adhesion, an adhesive, double-sided tape, ultrasonic fusion, laser welding, etc.

Hereinafter, exemplary microfluidic structures arranged within the platform 11 for use in a sample test will be described.

A sample may be a blend of a fluid and a particulate substance having a greater density than that of the fluid. For example, the sample may include a bodily sample, such as blood, salvia, urine and the like.

A sample chamber 20 may be defined in a radially inward location of the platform 11 to accommodate a predetermined amount of sample. At the top of the sample chamber 20, there is provided a sample injection port 14 through which a sample is introduced into the sample chamber 20.

In certain circumstances, it may be necessary to test only the fluid, rather than the entire sample, which may include both the fluid and the particulate substance. Thus, a sample separating chamber 30 may be provided radially at the outer side of the sample chamber 20 to centrifugally separate the sample via rotation of the platform 11.

In an exemplary embodiment, an extra sample chamber 35 may be provided at one side of the sample separating chamber 30. Thus, if excess sample is injected into the sample chamber 20, only a predetermined amount of the sample required for the test remains in the sample separating chamber 30 and the excess sample is accommodated in the extra sample chamber 35.

The sample separating chamber 30 includes a channel-shaped supernatant collecting region 31 radially outwardly extending from the sample chamber 20 and a sediment collecting region 32 radially at the outer side of the supernatant collecting region 31 to provide a space in which sediment having a relatively larger specific gravity may be accommodated. If the sample is blood, blood cells are collected in the sediment collecting region 32 and serum having a lower specific gravity than the blood cells is collected in the supernatant collecting region 31 during rotation of the platform 11. Thus, the blood is divided into blood cells and serum in the sample separating chamber 30, and the serum may be used for testing.

Then, the sample is introduced into a metering chamber 40 so as to be metered to a preset amount that is required for the test. Although FIG. 2 illustrates the metering chamber 40 as being connected to the sample separating chamber 30, the microfluidic device 10 may lack the sample separating chamber 30 and therefor, the metering chamber 40 may be directly connected to the sample chamber 20.

A residual sample removal chamber 50 may be provided around the metering chamber 40 to remove the excess sample after the sample has been metered by the metering chamber 40.

At least one dilution chamber 60 may be connected to the metering chamber 40 to receive a preset amount of sample. The at least one dilution chamber 60 may include a plurality of dilution chambers (e.g., 60a and 60b) in which different amounts of dilution buffer are stored respectively. The volume of the plurality of dilution chambers 60 may vary according to a required volume of dilution buffer. In one exemplary embodiment, the microfluidic device 10 includes first and second dilution chambers 60a and 60b in which different volumes of dilution buffer are accommodated respectively to exhibit different dilution ratios.

Additionally, a dilution chamber 61 may be provided within the platform such that no sample is supplied from the sample separating chamber 30 to the dilution chamber 61. The dilution chamber 61, to which no sample is supplied, functions to obtain a standard value (e.g., a positive and/or negative control) and is configured to accommodate a dilution buffer. A plurality of chambers 73 may be provided at the outer side of the dilution chamber 61 to which no sample is supplied. The chambers 73 may be empty or may be filled with distilled water and function to obtain a detection standard value.

A distribution channel 90 is connected to an exit of the dilution chamber 60. The distribution channel 90 includes a first section 91a extending from the exit of the dilution chamber 60 in a radial outward direction of the platform 11, and a second section 91b circumferentially extending from an outer end of the first section 91a. A distal end of the second section 91b may be connected to a vent (not shown). The vent (not shown) may be positioned to prevent leakage of the sample when the sample is transferred using centrifugal force from the dilution chamber 60 to the distribution channel 90. The distribution channel 90 may achieve a constant fluid resistance from a front end thereof connected to the exit of the dilution chamber 60 to a rear end thereof connected to the vent (not shown), i.e., throughout the entire section including the first section 91a and the second section 91b. To achieve the constant fluid resistance, the distribution channel 90 may have a constant cross sectional area. Thereby, rapid and effective distribution of the sample may be accomplished by excluding possible fluid movement resistance during distribution of the fluid to the maximum extent possible.

Reaction chamber groups 70a and 70b may be arranged at the outer side of the first and second dilution chambers 60a and 60b, respectively. Specifically, a first reaction chamber group 70a is provided at the outer side of the corresponding first dilution chamber 60a and a second reaction chamber group 70b is provided at the outer side of the corresponding second dilution chamber 60b.

Each reaction chamber group 70a or 70b includes at least one reaction chamber 71 or 72. The reaction chamber 71 or 72 is connected to the corresponding dilution chamber 60 through the distribution channel 90 that distributes the dilution buffer. In the simplest configuration, the reaction chamber group 70a or 70b may include a single reaction chamber.

The reaction chamber 71 or 72 may be a hermetic chamber. As used herein, the term "hermetic" means that each reaction chamber 71 or 72 has no vent for gas exhaust. Various kinds or concentrations of reagents, which cause optically detectable reactions with a sample dilution buffer distributed through the distribution channel 90, may be previously introduced into the plurality of reaction chamber 71 and 72. The reagents may be accommodated in a solid phase within the reaction chambers 71 and 72. Examples of optically detectable reactions include, but are not limited to, variation in fluorescence and/or optical density. However, the purposes of the reaction chambers 71 and 72 are not limited to the above.

In one exemplary embodiment, the plurality of reaction chambers 71 or 72 may store reagents suitable for reactions with the sample dilution buffer at the same dilution ratio.

For example, the first reaction chamber group 70a may store reagents, such as triglycerides (TRIG), total cholesterol (Chol), glucose (GLU), urea nitrogen (BUN), etc., which react under a dilution ratio (dilution buffer/sample) of 100. Likewise, the second reaction chamber group 70b may store reagents, such as direct trilirubin (DBIL), total bilirubin (TBIL), gamma glutamyl transferase (GGT), etc., which react under a dilution ratio (dilution buffer/sample) of 20.

In other words, if a sample dilution buffer, which is supplied from the second dilution chamber 60b to the plurality of reaction chambers 72 of the corresponding second reaction chamber group 70b, has a different dilution ratio than the first reaction chamber group 70a, the reaction chambers 71 and 72 of the reaction chamber groups 70a and 70b may respectively store reagents suitable for specific dilution ratios of the sample.

The reaction chambers 71 and 72 may have the same capacity, but are not limited as such. In embodiments in which different capacities of sample dilution buffer or reagent are required according to test items, the capacities of the reaction chambers 71 and 72 may differ from each other.

The plurality of reaction chambers 71 and 72 may be chambers provided with vents and injection ports.

The plurality of reaction chambers 71 and 72 are individually connected to the second section 91b of the distribution channel 90 through an entrance channel 92.

In an exemplary embodiment, channels connecting the respective chambers to each other may be provided with valves, e.g., 81, 82, 83 and 84. The valves 81, 82, 83 and 84 used herein may be normally closed valves. The valves 81, 82, 83 and 84 may include a first valve 81 provided at an exit side of the sample separating chamber 30, a second valve 82 provided at an entrance side of the residual sample removal chamber 50, a third valve 83 provided at an exit side of the metering chamber 40, and a fourth valve 84 disposed at an exit side of the dilution chamber 60 so as to open or close the distribution channel 90.

The respective valves 81, 82, 83 and 84 may be various kinds of valves, such as valves that are passively opened if a predetermined pressure or more is applied (like capillary valves), or valves that are actively operated upon receiving power or energy from the outside in response to actuation signals. In one exemplary embodiment, the microfluidic device 10 employs one or more phase transition valves that are operated by absorbing energy from an external source.

Each valve is positioned between upper and lower plates of the platform 11 and has a three-dimensional or planar shape as described above. The valve serves to block the flow of fluid and is melted at a high temperature to move into an adjacent clearance so as to open the channels.

To apply heat to the valves 81, 82, 83 and 84, an external energy source (322, see FIG. 6) to emit light is movably disposed at the outside of the platform 11. The external energy source 322 may irradiate light to sites where the valves 81, 82, 83 and 84 are located.

Figure 6:
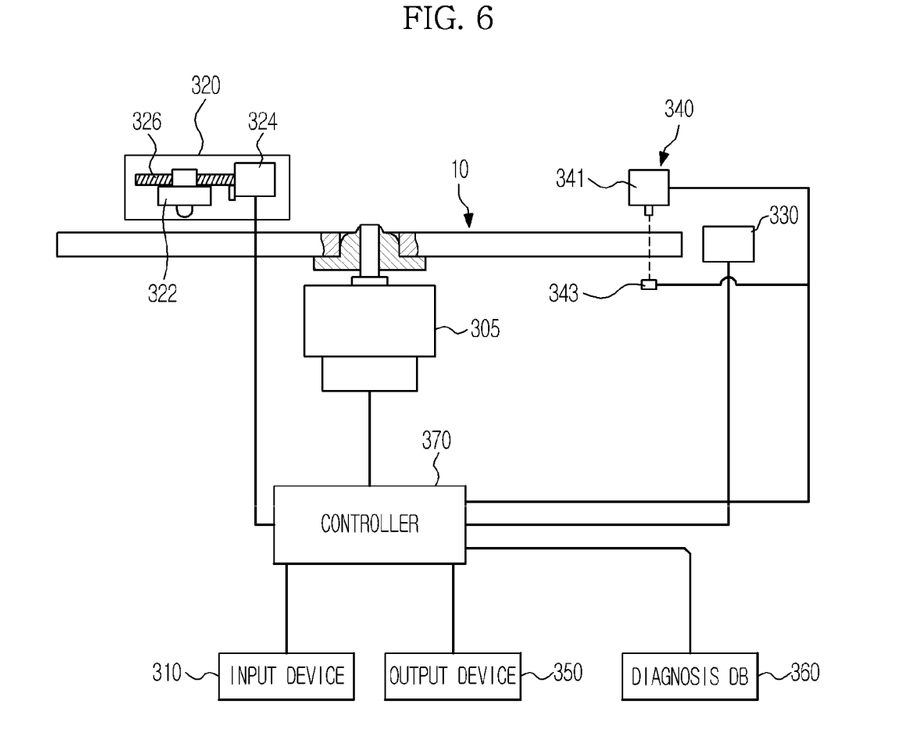
FIG. 6 is a diagram of a sample testing apparatus using a microfluidic device according to an exemplary embodiment.

Thus, the external energy source 322 is moved to above any one of the valves 81, 82, 83 and 84 that is necessary to be opened according to the test protocol of the disc-type microfluidic device 10, and irradiates light (or energy) onto the corresponding valve 81, 82, 83 or 84 for valve opening.

The valves 81, 82, 83 and 84 may be formed of a phase transition substance, with heat emitting particles, which absorb electromagnetic waves and then generate heat, distributed throughout the phase transition substance. In one exemplary embodiment, the valve material may include a phase transition material which is solid at room temperature, such as wax. The wax may be solid at room temperature and become liquid when it is heated. Exemplary waxes, include but are not limited to, paraffin wax, microcrystalline wax, synthetic wax, natural wax or the like.

The heat emitting particles may be sized to be freely movable within a channel having a width of several hundred to thousands of micrometers. If light (e.g., a laser) is irradiated onto the heat emitting particles, the temperature of the heat emitting particles rapidly increases. In order to exhibit the foregoing properties, each of the heat emitting particles may be formed from a metallic core and a hydrophobic shell. For example, the heat emitting particle may include an iron (Fe) core and a shell consisting of multiple surfactants bonded to the Fe core to enclose the Fe core. As an example of the heat emitting particles, commercially available ones distributed in a carrier oil may be adopted.

The heat emitting particles are not particularly limited to polymer particles, as provided herein for illustrative purposes. In another exemplary embodiment, the heat emitting particles may be in a quantum dot or magnetic bead form. In another exemplary embodiment, the heat emitting particles may be micro-metal oxides such as $Al_2O_3$, $TiO_2$, $Ta_2O_3$, $Fe_2O_3$, $Fe_3O_4$ or $HfO_2$.

In another exemplary embodiment, the heat emitting particles may be stored in a dispersion state in a carrier oil. The carrier oil may also be hydrophobic to allow the heat emitting particles having the hydrophobic surface structure to be uniformly dispersed in the carrier oil. Thus, a channel may be closed by forming a uniform dispersion of the melted transition material and the carrier oil containing the micro-heating particles, and introducing the mixture into the channel.

If the heat emitting particles convert absorbed energy into thermal energy, the particles rapidly heat up and transfer the thermal energy to the surrounding area. Thus, the wax is melted by the thermal energy, which results in collapse of the valve and opening of the channel. The wax may have a moderate melting point. If the melting point is excessively high, the period of time from energy irradiation to valve opening is excessively increased, which makes it difficult to accurately control valve opening time. On the contrary, if the melting point is excessively low, the wax may be partially melted in a state in which no light is irradiated, thereby causing fluid leakage.

In another exemplary embodiment, the phase transition substance may be a gel or thermoplastic resin. Gels may be selected from polyacrylamide, polyacrylates, polymethacrylates, polyvinylamides, or the like. Thermoplastic resins may be selected from cyclic olefin copolymer (COC), polymethylmethacrylate (PMMA), polycarbonate (PC), polystyrene (PS), polyoxymethylene acetal polymer (POM), perfluoroalkoxy copolymer (PFA), polyvinyl chloride (PVC), polypropylene (PP), polyethylene terephthalate (PET), polyetheretherketone (PEEK), polyamide (PA), polysulphone (PSU), polyvinylidene fluoride (PVDF) or the like.

In one exemplary embodiment, a barcode 13 may be provided at the lateral surface of the platform 11. The barcode 13 may store a variety of information as necessary, including, but not limited to, a date of manufacture, expiration date, etc.

The barcode 13 may be selected from various types of barcodes. For example, the barcode 13 may be of a one-dimensional barcode type, or of a two-dimensional barcode type (e.g., a matrix code) to store a great quantity of information.

In certain embodiments, the barcode 13 may be replaced by a hologram, radio frequency identification (RFID) tag, or memory chip, used to store information therein. In the case where the barcode 13 is replaced by a storage medium, such as, e.g., a memory chip to enable reading and writing of information, it may be possible to store identification information and other information related to sample testing results, patient information, blood collecting/testing date and time, and whether or not a test has been executed.

As described above, the microfluidic device 10 includes the plurality of chambers and the plurality of channels connecting the chambers to one another. During rotation of the platform 11, a fluid is discharged from the chamber through the channel connected to the chamber. The chamber has a discharge configuration to discharge all the fluid without leaving remnants in the chamber.

Figure 3:
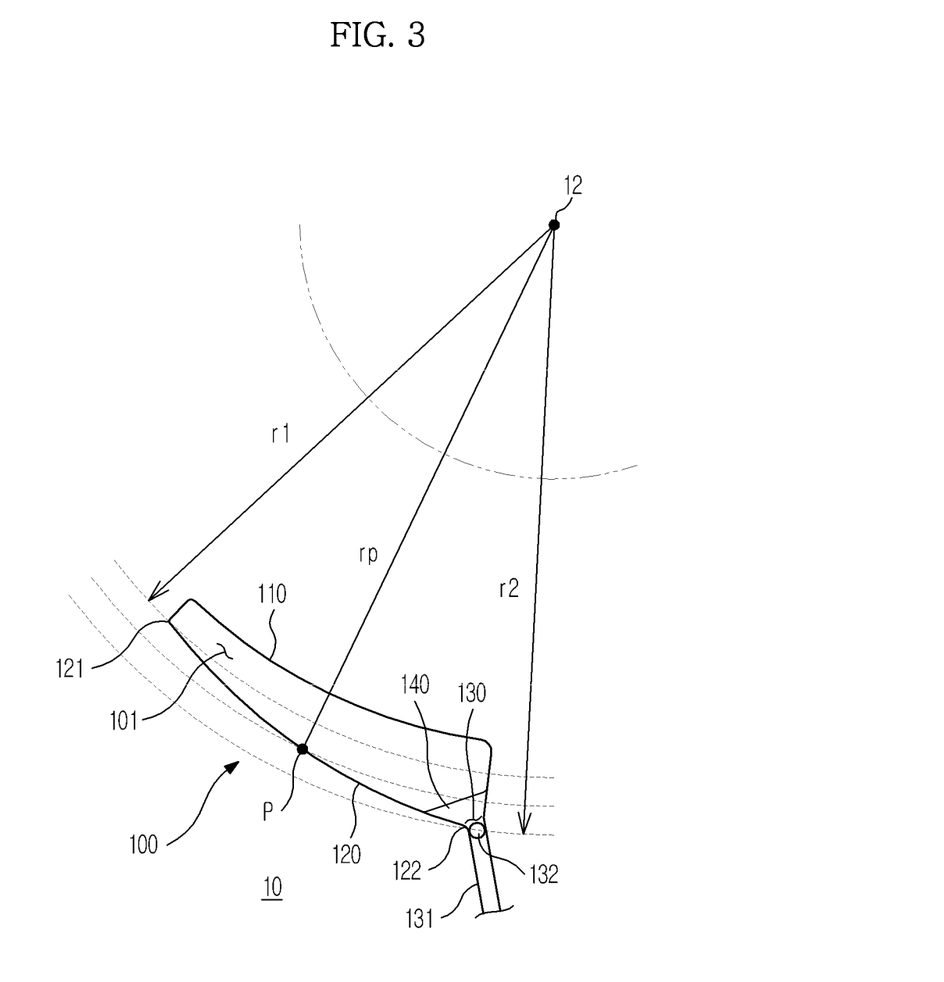
FIG. 3 is a plan view illustrating a discharge configuration of a chamber included in a microfluidic device according to an exemplary embodiment.
Figure 4:
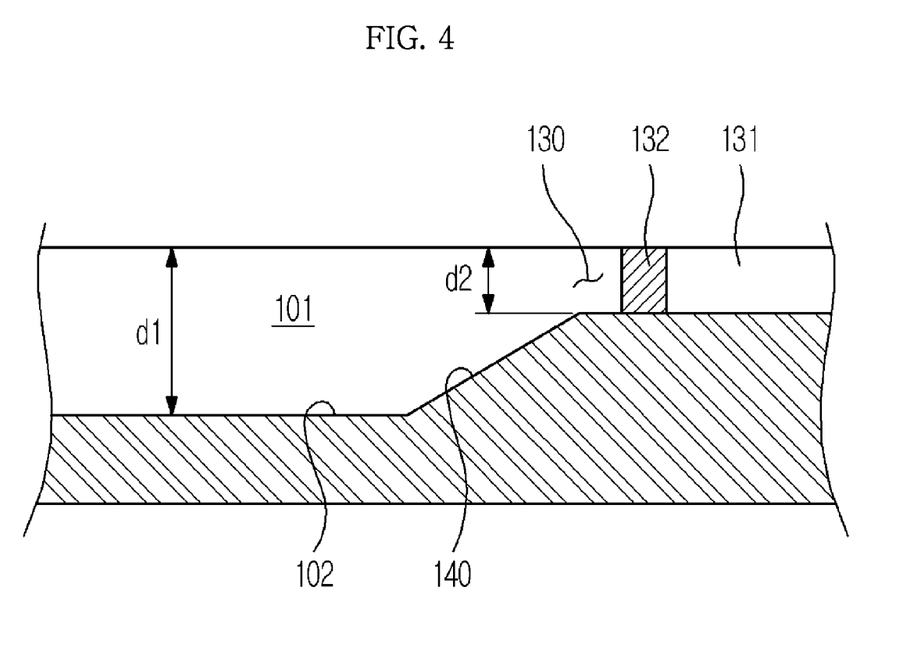
FIG. 4 is a cross sectional view illustrating an exemplary embodiment of the discharge configuration of the chamber.

FIG. 3 is a plan view illustrating a discharge configuration of a chamber included in a microfluidic device according to an exemplary embodiment, and FIG. 4 is a cross sectional view illustrating the discharge configuration of the chamber.

As illustrated in FIGS. 3 and 4, the chamber 100 includes an accommodation space 101 to accommodate a fluid therein, an inner sidewall 110 defining one sidewall of the accommodation space 101, an outer sidewall 120 defining the other opposite sidewall of the accommodation space 101, the outer sidewall 120 being located farther than the inner sidewall 110 radially from the rotational center of the platform 11, and an exit 130 through which the fluid exits the accommodation space 101.

The chamber 100 may have a fluid injection port (not shown), through which the fluid is introduced into the accommodation space 101 through the fluid injection port (not shown). In one example, the sample chamber 20 illustrated in FIG. 2 may be in fluid communication with the sample injection port 14 provided at the platform 11, and a sample may be injected into the sample chamber 20 by a fluid injector, such as a pipette, etc.

Alternatively, the chamber 100 may have an entrance (not shown) for fluid introduction. The entrance (not shown) may be connected to a fluid inlet channel (not shown) such that a fluid is introduced into the accommodation space 101 of the chamber 100 through the inlet channel (not shown) by centrifugal force generated during rotation of the platform 11. The entrance (not shown) may be formed at the inner sidewall 110 to allow the fluid to be introduced into the accommodation space 101 of the chamber 100 in a direction of centrifugal force.

The chamber 100 may have various shapes according to a required volume of the accommodation space 101 and functions of the chamber 100. In particular, since the platform 11 provided with the chamber 100 has a limited size, the chamber 100 may be shaped to utilize a space provided by the platform 11 to the maximum extent possible. Additionally, where centrifugal force by rotation of the platform 11 is utilized for fluid delivery force, a fluid is delivered outward in a radial direction of the platform 11. Thus in terms of space utility of the platform 11, the chamber 100, which is adapted to accommodate a great amount of fluid, may advantageously extend in the circumferential direction of the platform 11, as opposed to extending in the radial direction of the platform 11. As illustrated in FIGS. 3 and 4, the chamber 100 according to an exemplary embodiment has an arc shape and circumferentially extends at a predetermined radius from the rotational center of the platform 11.

The inner sidewall 110 extends in the circumferential direction of the platform 11. The length of the inner sidewall 110 may vary according to the required volume of the accommodation space 101. However, the chamber 100 may have various shapes and thus, the inner sidewall 110 also may have various shapes.

The outer sidewall 120 is outwardly spaced apart from the inner sidewall 110 in the radial direction of the platform 11. Thus, the fluid accommodated in the accommodation space 101 of the platform 11 moves to the outer sidewall 120 upon receiving centrifugal force by rotation of the platform 11.

On the basis of the rotational center 12 of the platform 11, a point closest to the outer sidewall 120 assumes a first point 121 and a point farthest from the outer sidewall 120 assumes a second point 122. The first point 121 and the second point 122 are located at opposite ends of the outer sidewall 120. A third point P is an arbitrary point between the first point 121 and the second point 122. Distances from the rotational center of the platform 11 to the first point 121, the second point 122 and the third point P are designated by r1, r2 and rp, respectively.

The second distance r2 is greater than the first distance r1. The third distance rp increases as the third point P is displaced from the first point 121 to the second point 122. Specifically, the distance from the rotational center of the platform 11 to an arbitrary point of the outer sidewall 120 increases as the arbitrary point is closer to the second point 122 or farther from the first point 121, i.e., r1≤rp≤r2. In other words, a distance from the rotational center of the platform 11 continuously increases along a length of the outer sidewall 120 from the first point 121 to the second point 122. Thus, the distance between the inner sidewall 110 and the outer sidewall 120 radially from the rotational center of the platform 11 increases from the first point 121 to the second point 122 because the inner sidewall 110 extends in a circumferential direction of the platform 11.

Centrifugal force applied to an arbitrary point P is proportional to the distance from the center of rotation to the arbitrary point P, i.e., a rotational radius. Therefore, centrifugal force applied to the fluid nearest to the second point 122 is greater than the centrifugal force applied to the fluid nearest the first point 121.

The exit 130 is located at the second point 122. The fluid near the first point 121 may move to the second point 122 along the outer sidewall 120 by centrifugal force and may exit the chamber 100 through the exit 130. As such, since the fluid receives the largest centrifugal force nearest the exit 130 located at the second point 122, the fluid within the accommodation space 101 of the platform 11 may flow out through the exit 130 without remaining in the accommodation space 101.

An exit channel 131 is connected to the exit 130. Although it is shown that the exit channel 131 extends in the radial direction of the platform 11 to guide the fluid radially outward of the platform 11, it should be understood that the exit channel 131 may extend in the circumferential direction of the platform 11 as necessary. Alternatively, the exit channel 131 may partially extend radially inward of the platform 11 to create a siphon effect. Additionally, an exit valve 132 may be provided at the exit channel 131 to control flow of the fluid.

In an exemplary embodiment, the accommodation space 101 of the chamber 100 has a first depth d1 and the exit 130 has a second depth d2, which less than the first depth d1 (see FIG. 4). Because of the difference between the depth of the accommodation space and the exit 130, the fluid on the bottom surface 102 of the chamber 100 may fail to be guided to the exit 130 during rotation of the platform 11. Thus, the chamber 100 has a slope 140 that is inclined upward from the bottom surface 102 to the exit 130.

With provision of the slope 140, the depth of the accommodation space 101 of the chamber 100 decreases approaching the exit 130. During rotation of the platform 11, the fluid on the bottom surface 102 of the chamber 100 may therefore be guided to the exit 130 along the slope 140.

If the exit channel 131 is opened and the platform 11 is rotated in a state in which the accommodation space 101 of the chamber 100 is full of fluid, the fluid flows out through the exit 130 by centrifugal force applied in a radial outward direction of the platform 11. The fluid may therefore be guided to the exit 130 along the outer sidewall 120 because the distance from the rotational center of the platform 11 to the outer sidewall 120 of the chamber 100 increases closer to the exit 130. Thereby, all the fluid may move to the exit 130 without remaining on the outer sidewall 120.

Additionally, even if a height difference exists between the bottom surface 102 of the chamber 100 and the exit 130, the slope 140 provided between the bottom surface 102 and the exit 130 allows the fluid to overcome the height difference and be guided to the exit 130.

Figure 5:
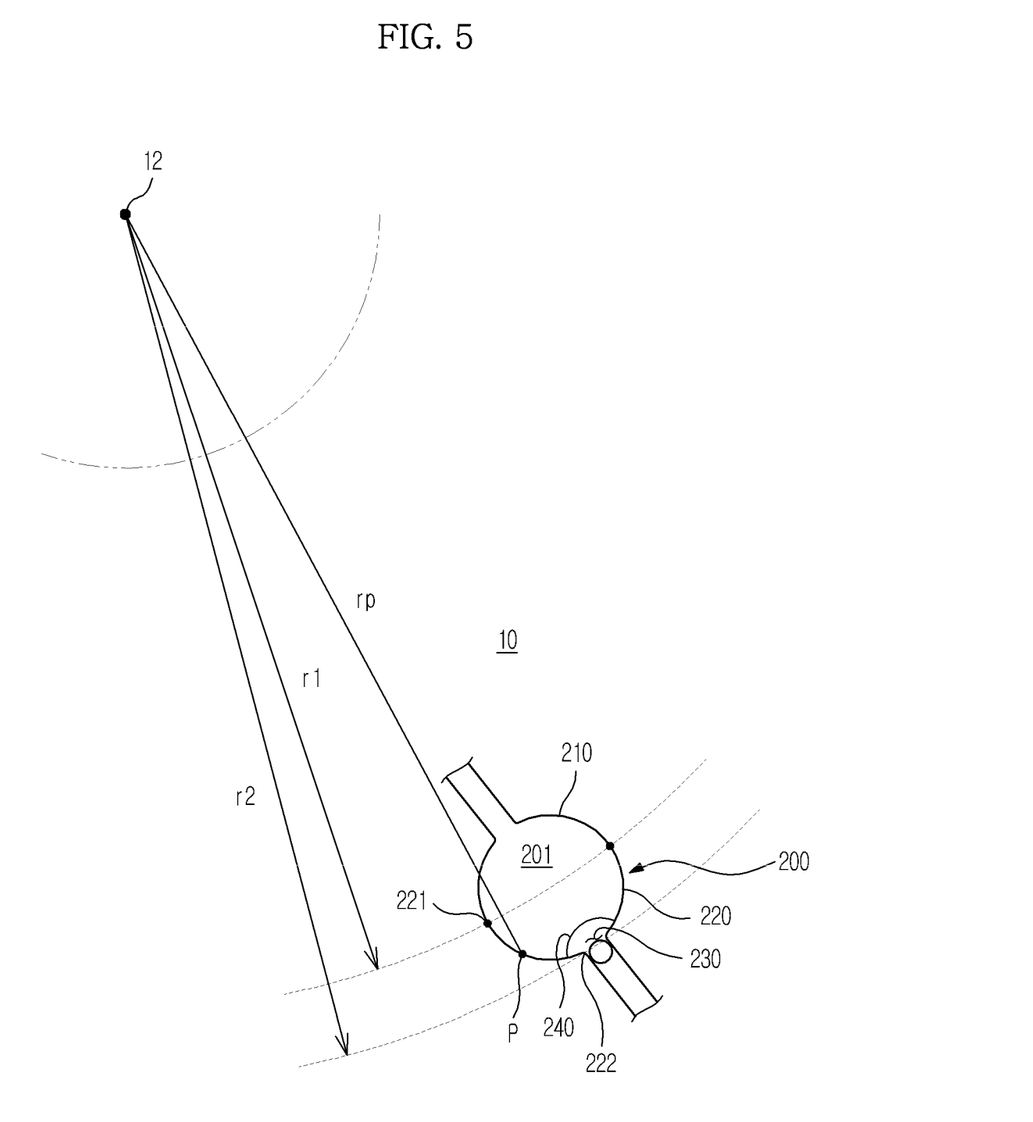
FIG. 5 is a plan view illustrating a discharge configuration of a chamber included in the microfluidic device according to another exemplary embodiment.

FIG. 5 is a plan view illustrating a discharge configuration of a chamber included in the microfluidic device according to another embodiment.

As illustrated in FIG. 5, the chamber 200 includes an accommodation space 201 to accommodate a fluid therein, an inner sidewall 210 defining one sidewall of the accommodation space 201, an outer sidewall 220 defining the other opposite sidewall of the accommodation space 201, the outer sidewall 220 being located radially farther than the inner sidewall 210 from the rotational center 12 of the platform 11, and an exit 230 through which the fluid exits the accommodation space 201.

Unlike the chamber 100 illustrated in FIGS. 3 and 4, the inner sidewall 210 and the outer sidewall 220 may be connected at ends thereof to each other.

The chamber 200 may be a metering chamber to meter a fluid to a preset amount. Reactions of a fluid occurring in a microfluidic device are often sensitive to the amount of the fluid used therein. For example, if the amount of a fluid is less than a preset amount required for reaction with a reagent, the reaction results may be erroneous.

The metering chamber may therefore be necessary to accommodate a preset accurate amount of fluid, and to discharge all of the fluid accommodated therein without the leaving remnants thereof.

The second distance r2 is greater than the first distance r1 and therefore, centrifugal force applied to the fluid nearer to a second point 222 where the exit 230 is located is greater than centrifugal force applied to the fluid nearer to a first point 221. A third distance rp from the rotational center 12 of the platform 11 to a third point P between the first point 221 and the second point 222 gradually increases from the first point 221 to the second point 222. Thus, the fluid may be guided to the exit 230 along the outer sidewall 220 during rotation of the platform 11. A slope 240 is provided at the bottom surface of the chamber 200 near the exit 230. Thereby, with a height difference between the bottom surface of the chamber 200 and a bottom surface of the exit 230, it may be possible to prevent the fluid from remaining near the exit 230, and thus emerge through the exit 230.

FIG. 6 is a diagram of a sample testing apparatus using a microfluidic device according to an exemplary embodiment.

The sample testing apparatus includes a spindle motor 305 to rotate the microfluidic device 10, a data reading device 330, a valve opening device 320, an inspection device 340, an input device 310, an output device 350, a diagnosis database (DB) 360, and a controller 370 to control the above mentioned devices.

The spindle motor 305 may initiate or stop rotation of the microfluidic device 10 to allow the microfluidic device 10 to reach a specific position.

Although not shown, the spindle motor 305 may include a motor drive device to control an angular position of the microfluidic device 10. For example, the motor drive device may utilize a step motor or DC motor.

The data reading device 330 may be, e.g., a barcode reader. The data reading device 330 reads data stored in the barcode 13 and transmits the data to the controller 270. The controller 370 operates the respective devices based on the read data, to drive the sample testing apparatus.

The valve opening device 320 is provided to open or close the valves of the microfluidic device 10. The valve opening device 320 may include the external energy source 322 and moving units 324 and 326 to move the external energy source 222 to any one of the valves that needs to be opened or closed.

The external energy source 322 to radiate electromagnetic waves may be a laser light source to irradiate laser beam, or may be a light emitting diode or xenon lamp to irradiate visible or infrared light. In particular, the laser light source may include at least one laser diode.

The moving units 324 and 326 serve to regulate the position or orientation of the external energy source 322, so as to allow the external energy source 322 to focus energy to a desired region of the microfluidic device, i.e., to the valve to be opened or closed. The moving units 324 and 326 may include a drive motor 324 and a gear 326 to move the external energy source 322 mounted thereon to a position above the valve to be opened or closed via rotation of the drive motor 324. The moving units may be realized via various mechanisms.

The inspection device 340 may include at least one light emitting element 341 and a light receiving element 343 arranged to correspond to the light emitting element 341.

Thus, the light receiving element 343 serves to receive light having passed through a reaction region of the microfluidic device 10.

The light emitting element 341 is a light source that can be turned on or off at a predetermined frequency. Exemplary light sources include, but are not limited to, semiconductor light emitting devices, such as Light Emitting Diodes (LEDs), Laser Diodes (LDs), etc., and gas discharge lamps, such as halogen lamps, xenon lamps, etc.

The light emitting element 341 is positioned to allow light emitted therefrom to reach the light receiving element 343 through the reaction region.

The light receiving element 343 is adapted to generate electric signals according to the intensity of incident light. For example, the light receiving element 243 may be a depletion layer photo diode, Avalanche Photo Diode (APD), PhotoMultiplier Tubes (PMT), or the like.

The controller 370 controls the spindle motor 305, data reading device 330, valve opening device 320, inspection device 340, etc., to assure effective operations of the sample testing apparatus. Also, the controller 370 searches the diagnosis DB 360 for comparative analysis between information detected from the inspection device 340 and the diagnosis DB 360, thereby testing for the presence of diseases of blood received in the reaction region on the microfluidic device 10.

The input device 310 serves to input the kind of the sample introduced into the microfluidic device 10 and/or possible testing items according to the kind of the injected sample, and may take the form of, for example, a touch screen provided at the sample testing apparatus.

The output device 350 serves to output the diagnosed results and the completion of operation. The output device 350 may be a visual output device, such as a Liquid Crystal Display (LCD), an audio output device, such as a speaker, or an audio-visual output device.

As is apparent from the above description, discharging of all fluid accommodated in a chamber without the leaving remnants may be possible because the distance from the rotational center of the platform to the outer sidewall of the chamber increases closer to the exit of the chamber. Thus, a preset amount of fluid may be utilized for a subsequent process.

Further, since all the fluid accommodated in the chamber is discharged, it may be possible to prevent erroneous test results caused when the amount of fluid used for a particular test that is sensitive to the amount of sample differs from a preset amount of fluid, thereby enhancing reliability in test results.

Although exemplary embodiments have been shown and described, it should be appreciated by those skilled in the art that changes may be made in these embodiments without departing from the principles and spirit of the inventive concept, the scope of which is defined in the claims and their equivalents.

What is claimed is:

1. A microfluidic device comprising:
   a platform comprising a chamber configured to accommodate a fluid therein, the chamber comprising:
   an inner sidewall;
   an outer sidewall disposed outwardly from the inner sidewall in a radial direction of the platform; and
   a bottom surface,
   wherein the outer sidewall includes a first point located closest to a center of the platform, a second point located farthest from the center of the platform,
   wherein the chamber further comprises an exit provided at the second point for outflow of the fluid accommodated in the chamber,
   wherein the bottom surface is inclined upward to the exit, and
   wherein a distance from the inner sidewall to an arbitrary third point on the outer sidewall between the first point and the second point increases in a radial direction from the first point to the second point, so that the fluid near the first point is guided to the second point by centrifugal force during rotation of the platform.

2. The microfluidic device according to claim 1, wherein the first point and the second point are located respectively at opposite ends of the outer sidewall.

3. The microfluidic device according to claim 1, wherein the chamber is a metering chamber configured to supply a predetermined amount of fluid to the outside.

4. The microfluidic device according to claim 1, wherein the inner sidewall of the chamber is formed along a circumference at a predetermined radius from the center of the platform.

5. The microfluidic device according to claim 1, wherein the inner sidewall is formed along a circumference at a predetermined radius from the center of the platform, and wherein a distance between the inner sidewall and the outer sidewall in the radial direction of the platform increases from the first point to the second point.

6. The microfluidic device according to claim 1, wherein centrifugal force applied to the second point is greater than centrifugal force applied to the first point during rotation of the platform.

7. The microfluidic device according to claim 1, wherein the distance from the inner sidewall to the arbitrary third point on the outer sidewall between the first point and the second point continuously increases in a radial direction from the first point to the second point.

8. A microfluidic device comprising:
   a disc-shaped platform comprising a chamber configured to accommodate a fluid therein,
   wherein the chamber comprises an outer sidewall defining an outer wall of the chamber in a radial direction of the platform,
   wherein a distance from a center of the platform to an arbitrary point on the outer sidewall increases from a first end of the outer sidewall to a second end of the outer sidewall, and
   wherein the chamber further comprises an exit provided at the second end of the outer wall and a depth of the exit is smaller than a depth of the chamber.

9. The microfluidic device according to claim 8, wherein the chamber is a metering chamber configured to enable outflow of a predetermined amount of fluid to the outside.

10. The microfluidic device according to claim 8, wherein the chamber has an arc shape extending in a circumference at a predetermined radius from the center.

11. The microfluidic device according to claim 8, wherein the chamber further comprises an inner sidewall located inward from the outer sidewall in the radial direction of the platform, the inner sidewall being formed along a circumference at a predetermined radius from the center,
   wherein a distance between the inner sidewall and the outer sidewall in the radial direction of the platform increases from the first end of the outer side wall to the second end of the outer sidewall.

12. The microfluidic device according to claim 11, wherein the distance from the inner sidewall to the arbitrary third point on the outer sidewall between the first point and the second point continuously increases in a radial direction from the first point to the second point.

13. A microfluidic device comprising:
a platform comprising a chamber configured to accommodate a fluid therein, the chamber including an inner sidewall and an outer sidewall disposed radially outward from the inner sidewall with respect to a center of the platform,
wherein the outer sidewall includes a first end and a second end, and a distance between the inner sidewall and the outer sidewall radially from the center of the platform continuously increases from the first end to the second end, and
wherein a depth of the chamber in a portion adjacent to an exit thereof decreases approaching the exit.

* * * * *